(12) United States Patent
Brackett et al.

(10) Patent No.: US 8,126,861 B2
(45) Date of Patent: Feb. 28, 2012

(54) SYSTEM AND METHOD FOR MANAGING LARGE DATA SETS

(75) Inventors: Charles Cameron Brackett, Overland Park, KS (US); Michael Randolph Harkavy, Kansas City, MO (US)

(73) Assignee: Cerner Innovation, Inc., Overland Park, KS (US)

( * ) Notice: Subject to any disclaimer, the term of this patent is extended or adjusted under 35 U.S.C. 154(b) by 1793 days.

(21) Appl. No.: 10/749,524

(22) Filed: Jan. 2, 2004

(65) Prior Publication Data

US 2005/0149534 A1 Jul. 7, 2005

(51) Int. Cl.
G06F 7/00 (2006.01)
G06F 15/16 (2006.01)
G06F 15/173 (2006.01)
(52) U.S. Cl. ......... 707/705; 707/752; 709/206; 709/224
(58) Field of Classification Search .................. 707/100, 707/705, 740, 752; 705/3; 711/213
See application file for complete search history.

(56) References Cited

U.S. PATENT DOCUMENTS

| | | | | |
|---|---|---|---|---|
| 5,381,539 A * | 1/1995 | Yanai et al. | 711/133 |
| 5,586,262 A * | 12/1996 | Komatsu et al. | 705/2 |
| 5,649,153 A * | 7/1997 | McNutt et al. | 711/118 |
| 5,946,682 A * | 8/1999 | Wolfe | 1/1 |
| 6,032,120 A * | 2/2000 | Rock et al. | 705/2 |
| 6,115,486 A * | 9/2000 | Cantoni | 382/128 |
| 6,243,755 B1 * | 6/2001 | Takagi et al. | 709/229 |
| 6,308,158 B1 * | 10/2001 | Kuhnen et al. | 704/275 |
| 6,339,767 B1 * | 1/2002 | Rivette et al. | 707/781 |
| 6,496,716 B1 * | 12/2002 | Langer et al. | 600/425 |
| 6,574,629 B1 * | 6/2003 | Cooke et al. | 1/1 |
| 6,697,067 B1 * | 2/2004 | Callahan et al. | 345/427 |
| 6,891,920 B1 * | 5/2005 | Minyard et al. | 378/37 |
| 6,953,433 B2 * | 10/2005 | Kerby et al. | 600/443 |
| 6,999,614 B1 * | 2/2006 | Bakker et al. | 382/159 |
| 7,212,661 B2 * | 5/2007 | Samara et al. | 382/131 |
| 7,290,011 B2 * | 10/2007 | Eldar et al. | 707/693 |
| 7,729,597 B2 * | 6/2010 | Wright et al. | 386/125 |
| 2002/0016718 A1 * | 2/2002 | Rothschild et al. | 705/2 |
| 2002/0073429 A1 * | 6/2002 | Beane et al. | 725/105 |
| 2002/0082948 A1 * | 6/2002 | Panelli | 705/27 |
| 2002/0099569 A1 * | 7/2002 | Thirsk | 705/2 |
| 2002/0184325 A1 * | 12/2002 | Killcommons et al. | 709/206 |
| 2002/0186899 A1 * | 12/2002 | Bohnenkamp | 382/305 |
| 2002/0188474 A1 * | 12/2002 | Collamore et al. | 705/3 |
| 2002/0198991 A1 * | 12/2002 | Gopalakrishnan et al. | 709/225 |
| 2003/0041106 A1 * | 2/2003 | Tuli | 709/203 |
| 2004/0044547 A1 * | 3/2004 | Klennert et al. | 705/2 |
| 2005/0050552 A1 * | 3/2005 | Fuller | 719/321 |
| 2005/0086344 A1 * | 4/2005 | Suesserman | 709/227 |

* cited by examiner

Primary Examiner — Robert Timblin
(74) Attorney, Agent, or Firm — Shook Hardy & Bacon LLP

(57) ABSTRACT

The present invention is directed to a method and system for managing large data sets (or studies) transferred from at least one acquisition device to a study process server in order to transfer the data sets to at least one review station. The method includes transferring a selected subset of the existing data sets to each review station, monitoring each review station for a login, and populating the review station with studies from at least one relevant working set upon detecting the login. In an alternate embodiment, the method may include sorting each received study into an appropriate working set, selecting a subset of the collected set of studies from at least one working set, and distributing the selected subset of studies to each review station.

18 Claims, 5 Drawing Sheets

SYSTEM AND METHOD FOR MANAGING LARGE DATA SETS

CROSS-REFERENCE TO RELATED APPLICATIONS

None.

STATEMENT REGARDING FEDERALLY SPONSORED RESEARCH OR DEVELOPMENT

None.

TECHNICAL FIELD

Embodiments of the present invention relate to management of large data sets within a medical environment. More particularly, embodiments of the invention are directed to facilitating management of image data sets to provide immediate access to the image data sets within an automated medical environment.

BACKGROUND OF THE INVENTION

Currently, imaging data is captured at an image capturing location during a patient examination. Typically, a number of data sets or studies are created by the image acquisition device. These studies will later be reviewed on demand at a review station, likely having a location that is not yet determined. Accordingly, the captured data is stored in a central server location such as a picture archiving communication system (PACS) until it is requested by a reviewer.

In the field of medical imaging, modern techniques have created large data sets that can be cumbersome to transfer and store. Specialists including cardiologists need motion pictures at thirty or more frames per second. Each frame could be several megabytes or more in size. X-ray Angiography studies can average around one gigabyte or more.

When a physician is ready to review the studies, the physician will go to a review station to read and analyze the studies. Physicians may require that the study be available for reading immediately upon demand. Because of the large size of the data sets and the limited speed of hospital networks, simply retrieving the studies on demand may yield unacceptably long waiting times for physicians.

Several solutions have been proposed to the aforementioned problem. One solution is for the central data server to auto re-route the collected studies to all diagnostic stations. While this solution makes the images immediately available to physicians, it causes excessive network traffic and consumes a large amount of disk space.

Another solution created to solve this problem has been to automatically route the studies to a small set of review stations based on predictive algorithms. This solution also has drawbacks. For instance, if a physician selects a review station that was not predicted by the predictive algorithm, the physician may be required to wait an excessive amount of time for all of the studies to download. Alternatively, the physician may be forced to find a review station where the predictive algorithm routed the studies. Additionally, those stations selected by the predictive algorithm lose valuable storage space.

Accordingly, a solution is needed for making the large data sets available to the physician that does not require predicting physician location. A solution is also needed that does not auto-route all data sets to all review stations, thus creating excessive network traffic and consuming excessive memory resources.

BRIEF SUMMARY OF THE INVENTION

In one aspect, the present invention is directed to a method for managing large data sets (or studies) transferred from at least one acquisition device to a study process server in order to transfer the data sets to at least one review station. The method includes sorting each received study into appropriate working sets, selecting a subset of studies from at least one working set, and distributing the selected subset of studies to at least one review station.

In an additional aspect of the invention, a method is provided for managing large data sets transferred from at least one acquisition device to a study process server in order to transfer the data sets to at least one review station. The method includes transferring a selected subset of the existing data sets from the study process server to each review station and monitoring each review station for selected user activities, for example a login. The method additionally includes populating the review station with studies from a relevant working set upon detecting the selected user activities.

In an additional aspect of the invention, a system is provided for managing large data sets transferred from at least one acquisition device to a study process server in order to transfer the data sets to at least one review station. The system includes a study sorting module for sorting each study received by the study process server into an appropriate working set and a study control module for selecting a subset of studies from at least one working set. The system additionally includes a study distribution module for distributing the selected subset of studies to each review station.

In yet an additional aspect of the invention, a system is provided for managing large data sets transferred from at least one acquisition device to a study process server in order to transfer the data sets to at least one review station. The system includes a study distribution module for transferring a selected subset of the existing data sets to at least one review station and a study control module for monitoring each review station for selected user activities. The study distribution module populates the review station with studies from at least one relevant working set upon detection of the user activities by the study control module.

BRIEF DESCRIPTION OF THE DRAWINGS

The present invention is described in detail below with reference to the attached drawings figures, wherein.

DETAILED DESCRIPTION OF THE INVENTION

Embodiments of the present invention are directed to a system and method for managing large data sets to maximize efficiency. In particular, the system manages transfer of large data sets to review stations for physician viewing. Techniques of this invention optimize network and disk space utilization while satisfying the need for cardiology images on demand.

As will be further explained in conjunction with the FIGs. below, the system of the invention may prime all work review stations with a small set of studies, so that when a physician does log in, he can begin reading while the system then begins to retrieve more studies to be read.

Figure 1:
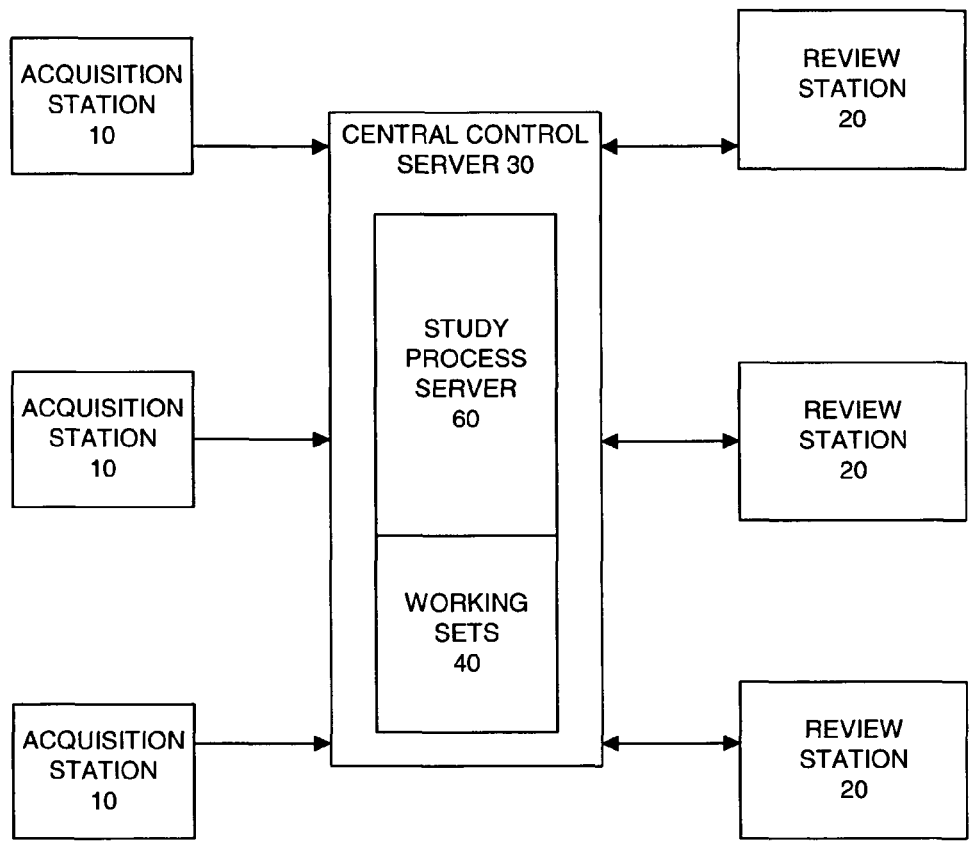
FIG. 1 is a block diagram illustrating components of a system for managing large data sets in accordance with an embodiment of the invention.

FIG. 1 illustrates a system for managing large data sets in accordance with an embodiment of the invention. Multiple acquisition devices 10 capture data and transmit the data over a network to a central control server 30. The central control server 30 preferably includes a study process server 60 and stored working sets 40. The working sets 40 are preferably stored in a database 150 as described below with respect to FIG. 2. The study process server 60 controls the distribution of the data stored in the working sets 40 over a network to a plurality of review stations 20, where physicians will be able to review the studies. The review stations may be diagnostic or non-diagnostic. The study process server 60 may prime each review station 20 with a number of studies so that a physician will have studies available for review on demand.

The study process server 60 creates the subset of distributed studies in any one of a number of ways that will be further explained below. By priming the review stations 20, the system of the invention gives the physician a starting set, while additional studies load in the background. When a physician logs in at any given review station 20, the study process server 60 knows where the reading and documentation will be done. As the review station 20 is already primed with a set of studies to review, the physician has studies on demand to begin working.

To accomplish the aforementioned goal, the central control server 30 tracks the studies that need to be reviewed in a working set. As explained further below, components of the central control server 30 then distribute studies from the working set across all review stations 20 so that each station has some studies from the working set. The system of the invention can customize the degree of replication of studies across different review stations and the fraction of the working set distributed can be customized to the capacity of the underlying network and storage systems as well as the typical work patterns of the readers.

Figure 2:
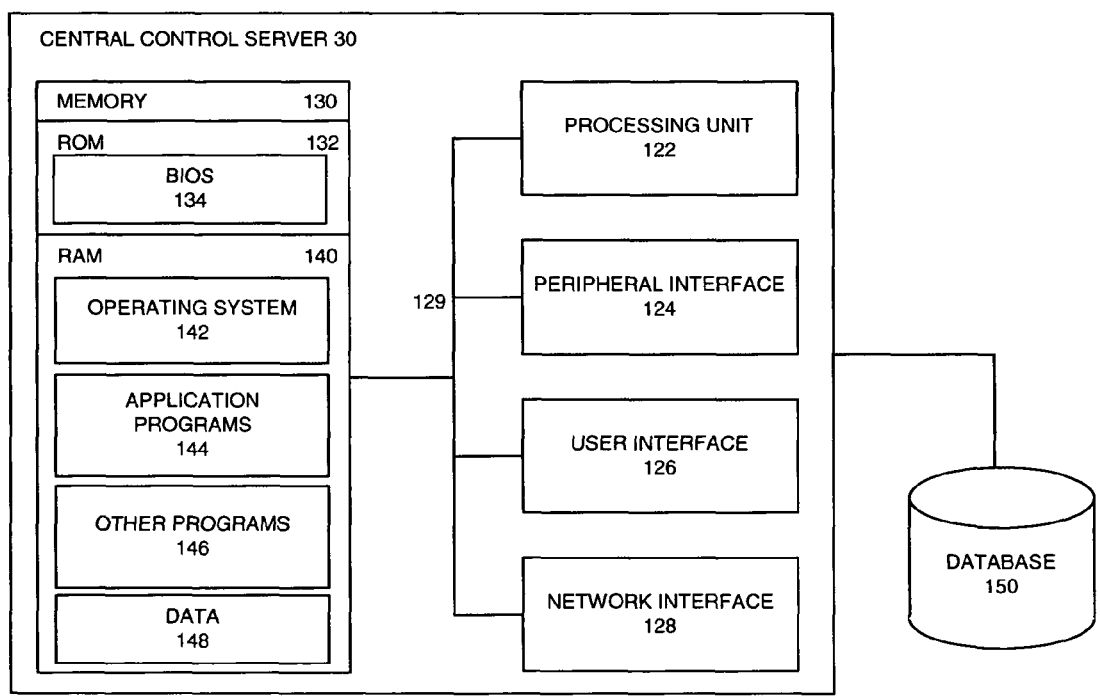
FIG. 2 is a block diagram illustrating components of a central control server in accordance with an embodiment of the invention.

FIG. 2 illustrates an embodiment of the components of the central control server 30. The central control server 30 may include a processing unit 122, a peripheral interface 124, a user interface 126, and a network interface 128. The central control server 30 may also include a memory 130. A system bus 129 couples the aforementioned components. The central control server 30 may also include a database 150.

The system memory 130 may include computer storage media in the form of volatile and/or nonvolatile memory such as read only memory (ROM) 132 and random access memory (RAM) 140. A basic input/output system 134 (BIOS), containing the basic routines that help to transfer information between elements within the central control server 30, such as during start-up, is typically stored in ROM 132. RAM 140 typically contains data and/or program modules that are immediately accessible to and/or presently being operated on by processing unit 122. For instance, the study process server 60 may be contained within the RAM 140 of the system memory 130.

By way of example, and not limitation, FIG. 2 illustrates operating system 142, application programs 144, other program modules 146, and program data 148. The application programs 144 and other programs 146 may be described in the general context of computer-executable instructions, such as program modules, being executed by a computer. Generally, program modules include routines, programs, objects, components, data structures, etc. that perform particular tasks or implement particular abstract data types. Moreover, those skilled in the art will appreciate that the invention may be practiced with other computer system configurations, including hand-held devices, multiprocessor systems, microprocessor-based or programmable consumer electronics, minicomputers, mainframe computers, and the like.

The central control server 30 may also include other removable/non-removable, volatile/nonvolatile computer storage media. A hard disk drive may be provided that reads from or writes to non-removable, nonvolatile magnetic media, a magnetic disk drive that reads from or writes to a removable, nonvolatile magnetic disk, and an optical disk drive that reads from or writes to a removable, nonvolatile optical disk such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive is typically connected to the system bus through a non-removable memory interface and magnetic disk drive and optical disk drive are typically connected to the system bus by a removable memory interface.

A user may enter commands and information into the central information system through the user interface 126 using input devices such as a keyboard and pointing device, commonly referred to as a mouse, trackball or touch pad. Other input devices may include a microphone, satellite dish, scanner, or the like. These and other input devices are often connected to the processing unit 122 through a user input interface 126 that is coupled to the system bus 129, but may be connected by other interface and bus structures, such as a parallel port or a universal serial bus (USB). A monitor or other type of display device may also be connected to the system bus 129 via an interface, such as the peripheral interface 124. In addition to the monitor, computers may also include other peripheral output devices such as speakers and printer.

The illustrated server system 30 is merely an example of a suitable environment for the system of the invention and is not intended to suggest any limitation as to the scope of use or functionality of the invention. Neither should the server system 30 be interpreted as having any dependency or requirement relating to any one or combination of components illustrated.

The server system 30 in the present invention may operate in a networked environment using logical connections to communicate with the components shown in FIG. 2. Logical connections for networking may include a local area network (LAN) or a wide area network (WAN), but may also include other networks. When used in a LAN networking environment, the server system 30 may be connected to the LAN through the network interface 128 or adapter. When used in a WAN networking environment, the server system 30 typically includes a modem or other means for establishing communications, such as the Internet. The modem, which may be internal or external, may be connected to the system bus 129 via the user input interface 126, or other appropriate mechanism.

Figure 3:
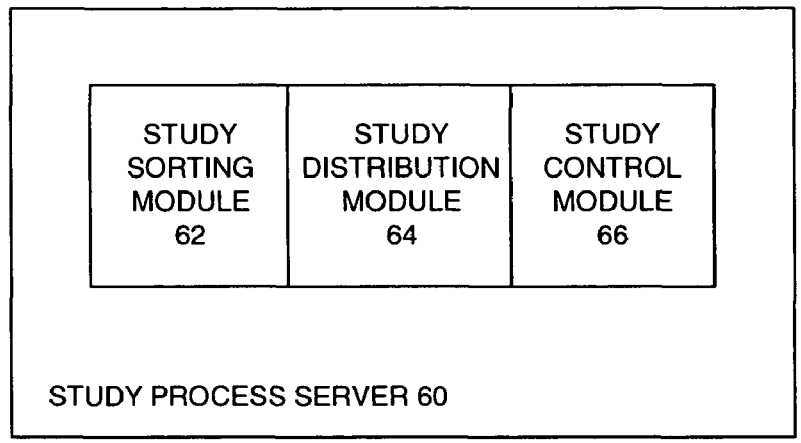
FIG. 3 is a block diagram illustrating components of a study process server in accordance with an embodiment of the invention.

FIG. 3 illustrates an embodiment of the components of the study process server 60. The study process server 60 may include a study sorting module 62, a study distribution module 64, and a study control module 66. The study sorting module 62 may receive the studies from the imaging stations 10 and sort them into appropriate working sets 40. The study distribution module 64 may distribute studies to the review stations 20. The study control module 66 may determine which studies should be grouped together for distribution and additionally may control further study processing.

Figure 4:
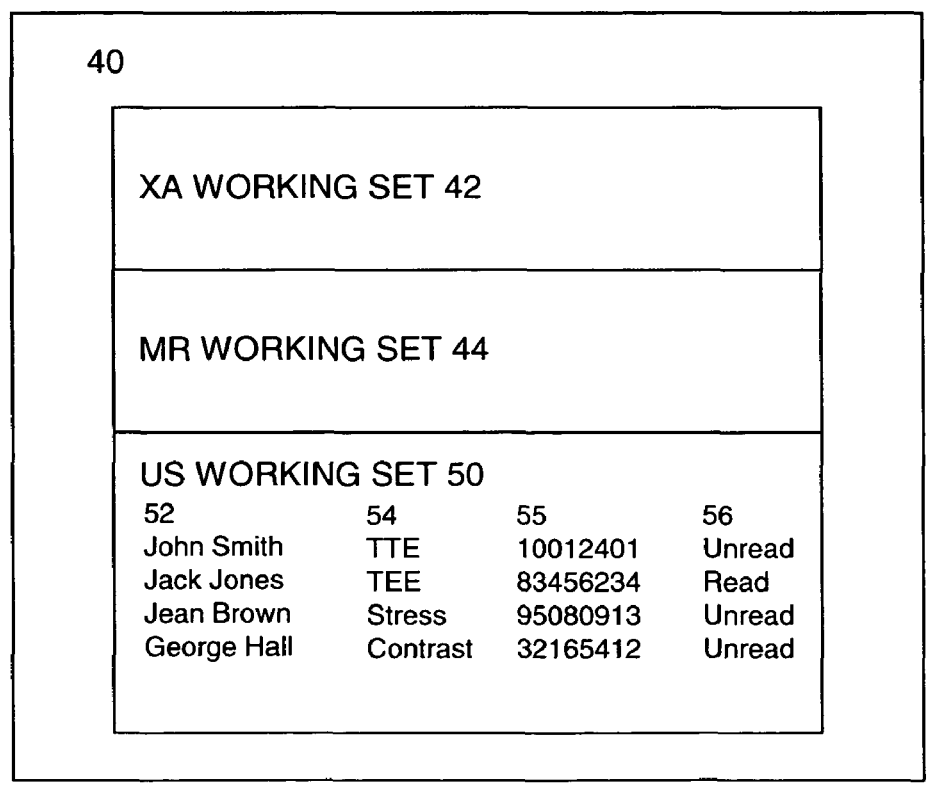
FIG. 4 is a block diagram illustrating components of a working set associated with a central control server in accordance with an embodiment of the invention.

FIG. 4 illustrates storage of the working sets 40. The working sets may include for example an XA (x-ray angiography) working set 42, an MR (magnetic resonance) working set 44, and a US (ultrasound) working set 50. Other examples include CR (computed radiography), CT (computed tomography), DR (digital radiography), NM (nuclear medicine) working sets. Each working set may include a plurality of studies. Each study may be associated with a patient name 52, a type of study 54, a unique study ID 55, and an indication of the study status 56. More generally, studies may be sorted into a working set based on the application of a number of parameters against any of a number of known characteristics for each study in addition to study type, status and patient name. By way of example and not limitation, the size of the study, facility at which the study was taken and time of the study may be evaluated to sort the study into one or more working sets. Studies that have been completed may ultimately be removed from a working set. A working set may be defined as a set of studies that has not been "completed". In order for a study to be completed, the system may require that one or more concerned parties have reviewed and analyzed the study.

In the illustrated embodiment, the working sets 40 are stored on the study process server 60. However, the working sets 40 may be stored at an alternative location and merely accessed in accordance with instructions stored on the study process server 60. The study ID 55 may include a distinct number for identification of each study. In an embodiment of the invention, the study ID is a 64 byte number. Furthermore, some studies may be stored in more than one working set. For example, a physician working set may be created that includes studies that are also included in the working set of another physician who requires access to the studies.

For the particular central control server 30 and set of reviewers, there may be multiple working sets and different reading roles all being processed with parameters and preferences set according to the workflow properties of the studies in that particular working set. For example, the reading roles and patterns of US (echo) studies may be different from those of XA studies. Accordingly, these studies would be stored in different working sets and the study control module 66 would use different rules to handle the different working sets.

In operation, imaging occurs at the acquisition devices 10 after an order has been created for a patient. When a patient arrives for an appointment, the patient is directed to an appropriate acquisition device 10 and the imaging process is performed. The subsequent steps are described below with reference to FIGS. 5 and 6.

Figure 5:
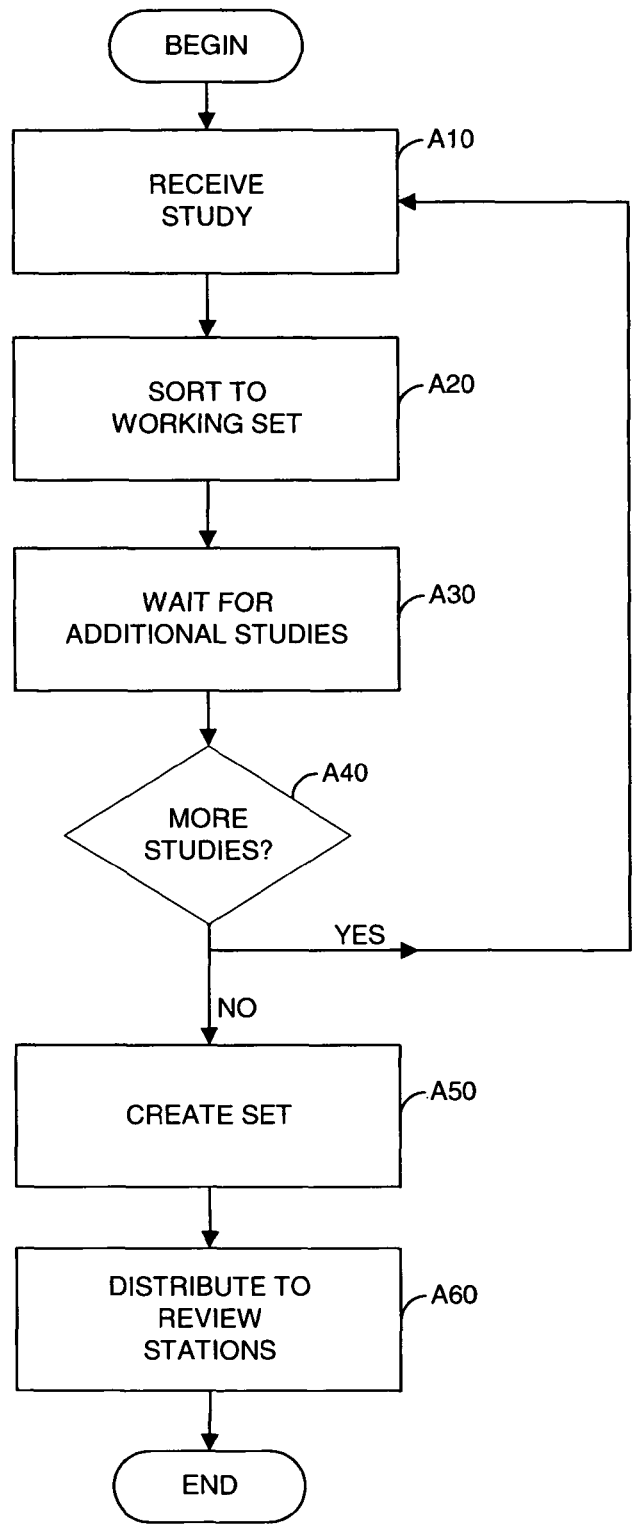
FIG. 5 is a flow chart illustrating a method for transferring data to a review station in accordance with an embodiment of the invention.

FIG. 5 is a flow chart illustrating a method in accordance with an embodiment of the invention. In step A10, the central control server 30 or other storage device receives one or more studies from the acquisition devices 10. It is possible to store the studies in an alternative device and process the studies using the instructions stored on the study process server 60. In step A20, the study sorting module 62 sorts each received study to one of the working sets 40. The central control server 30 waits for additional studies from the imaging stations 10 in step A30. If more studies are available in step A40, the central control server 30 or other storage device receives and sorts the studies. In step A50, the study control module 66 creates a subset of studies appropriate for distribution to each review station 20. In step A60, the study distribution module 64 distributes the created subset to the review stations 20.

The determination of the appropriate subset of studies for distribution in step A50 may be accomplished in a number of ways. In its most basic form, distribution or priming is accomplished "blindly" in that each review station 20 will receive the same subset of the entire set of studies received by the central control server 30. Typically, this subset will include the most recently acquired studies. The use of a subset rather than the entire set of studies received by the central control server 30 prevents excessive network traffic and excessive consumption of storage space.

Alternatively, the subset may be selected based on an algorithm within the study control module 66. The algorithm may be either a predictive or a non-predictive algorithm. A non-predictive algorithm would intelligently select a subset of data based on the central control server's working sets, procedure types, and schedules. For instance, a non-predictive algorithm might take a fixed number of studies from each working set, from each procedure type, or assigned to each physician. Alternatively, predictive algorithms may be used by the study control module 66. Predictive algorithms can determine appropriate review stations for distribution based on the physician schedule and defined working locations. This information may be stored in the central control server 30. The predictive algorithms may cause the distribution module 64 to distribute a larger subset of received studies to specifically predicted locations.

Although step A50 is directed to selecting a single subset, it should be understood that the study process server may select multiple subsets in step A50. Depending on the particular embodiment of the invention employed, different subsets may be directed to different review stations or all of the review stations may receive the same subsets. Furthermore, the selected subset or subsets may be selected from a single working set or from multiple working sets.

Figure 6:
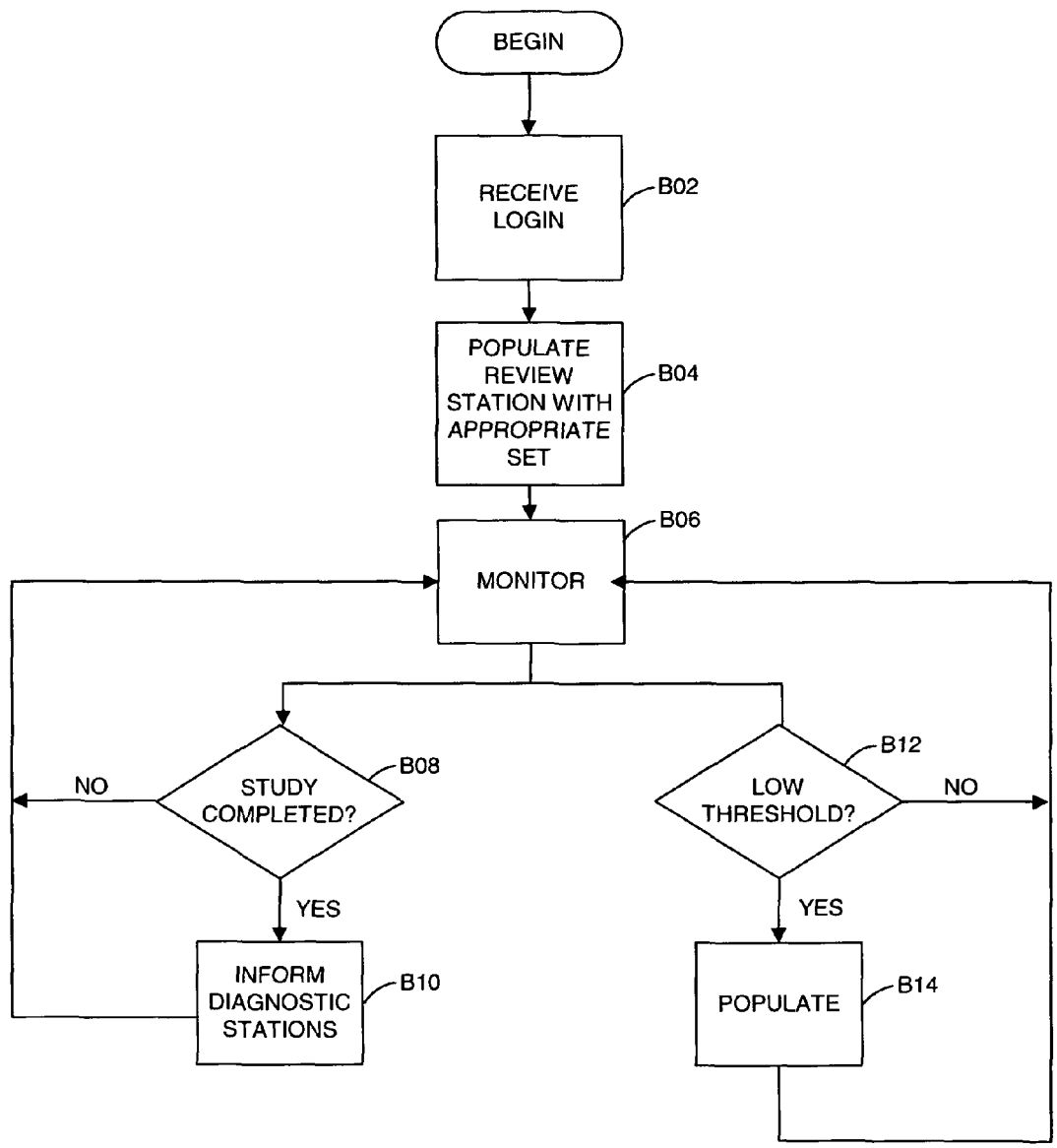
FIG. 6 is a flow chart illustrating further aspects of a method for transferring data to review stations in accordance with an embodiment of the invention.

As illustrated in FIG. 6, when a physician needs to access studies, he logs into a review station 20. Upon receiving a login (from a physician or other medical professional) in step B02, the study process server 60 populates the review station 20 with an appropriate data set for the physician in step B04. Once the study control module 66 knows from which review station 20 a physician is working, the study control module 66 can then begin filling that review station's buffer with more studies to view. The size of a particular buffer on a review station may be determined by the study control module 66 based on various factors including the presence of a reader for this type of study at this or other review stations, the speed at which the readers are progressing, and the congestion of the network.

In step B06, the study process server 60 continues to monitor activity at the review stations 20. In step B08, if a review station 20 informs the study process server 60 that a study has been completed, the study process server 60 informs other review stations 20 that the study has been completed in step B10 so that the other review stations 20 may delete the completed study in order to create space for additional studies. Furthermore, the study process server 60 may monitor the review stations 20 for a low buffer threshold in step B12. If a number of studies has been completed and deleted, the study process server 60 may re-populate the review station 20 in step B14.

As set forth above, a reader completes the work on a particular study, the study control module 66 is notified and may remove the study from the working set. Additionally, if the study completed on one review station also resides on another review station, the study control module 66 sends a message to that review station instructing it to delete that study in order to create space for another study. If the deletion of that study results in the buffer being too small, one or more replacement studies are automatically forwarded.

The review stations 20 may have pre-set "watermarks" or buffer thresholds. The review stations 20 preferably have a low watermark. If the low watermark is reached, the study process server 60 re-populates the review station 20 as described above. The watermark may be dynamic as it may grow and shrink based on the rate at which a physician reads studies on a particular diagnostic station. Alternatively, the watermark may be configurable. A configurable watermark could be pre-set for optimization based on the physician, procedure, network bandwidth, disk space, etc.

As described above, the system provides a technique for displaying large image data sets required to be displayed on demand in a distributed environment. A distinct advantage of the system is its reduction in network traffic and excessive disk space requirements while preventing imaging reading delays. The above-described system additionally reduces the need to upgrade network and disk infrastructures.

While particular embodiments of the invention have been illustrated and described in detail herein, it should be understood that various changes and modifications might be made to the invention without departing from the scope and intent of the invention. For instance, while the invention has generally been described in terms of a central server at which the studies are stored and subsets of the working sets are distributed, in embodiments the studies may be stored at one or more locations distinct from the central server. In these embodiments, the central server would direct the distribution of the studies in accordance with the invention from the distinct storage locations to the viewing stations. For example, a particular department may have its own PACS system at which studies are stored rather than transferring the studies to a central server. Instead, the departmental PACs would communicate information about the studies to the central server required to determine which studies should be distribute to which viewing stations and provide such instructions to the departmental PACS. The embodiments described herein are intended in all respects to be illustrative rather than restrictive. Alternate embodiments will become apparent to those skilled in the art to which the present invention pertains without departing from its scope.

From the foregoing it will be seen that this invention is one well adapted to attain all the ends and objects set forth above, together with other advantages, which are obvious and inherent to the system and method. It will be understood that certain features and sub-combinations are of utility and may be employed without reference to other features and sub-combinations. This is contemplated and within the scope of the appended claims.

What is claimed is:

1. A computerized method for managing studies transferred from at least one acquisition device to a study process server in order to transfer the studies to at least one review station, the computerized method comprising:

without having previously distributed the studies to a review station:
automatically sorting the studies into a plurality of working sets at the study process server, each working set comprising a collection of studies ready for review by at least one clinician as a set, wherein all studies within each working set are ready for delivery for review by the at least one clinician,
automatically selecting a subset of studies from a first working set to be transferred to a review station, and
automatically transferring the subset of studies from the first working set from the study process server to the review station such that the subset of studies from the first working set is available for review at the review station upon detecting a login, while delaying transfer of remaining studies in the first working set until clinician review of the subset of studies from the first working set at the review station is detected;
after completing transfer of the subset of studies from the first working set to the review station, monitoring the review station for clinician review of the subset of studies from the first working set;
detecting a clinician reviewing the subset of studies from the first working set at the review station; and
populating the review station with additional studies from the first working set in response to detecting the clinician reviewing the subset of studies from the first working set at the review station.

2. The method of claim 1, further comprising distributing the subset of studies from the first working set to each of a plurality of review stations.

3. The method of claim 1, further comprising implementing a predictive algorithm to identify a set of review stations and distributing the subset of studies from the first working set to the identified review stations.

4. The method of claim 1, further comprising continuously monitoring the review station to determine if review of a study from the first working set has been completed and removing the study from the first working set after review of the study has been completed at the review station.

5. The method of claim 4, further comprising deleting the study from at least one other review station in response to determining that review of the study has been completed at the review station.

6. The method of claim 1, further comprising monitoring the review station for a low buffer threshold and re-populating the review station with an additional subset of studies upon reaching the low buffer threshold.

7. One or more computer storage media storing computer-useable instruction that, when used by a computing device, cause the computing device to perform a computerized method for managing studies transferred from at least one acquisition device to a study process server in order to transfer the studies to at least one review station, the computerized method comprising:

without having previously distributed the studies to a review station:
automatically sorting the studies into a plurality of working sets at the study process server, each working set comprising a collection of studies ready for review by at least one clinician as a set, wherein all studies within each working set are ready for delivery for review by the at least one clinician,
automatically selecting a subset of studies from a first working set to be transferred to a review station, and
automatically transferring the subset of studies from the first working set from the study process server to the review station such that the subset of studies from the first working set is available for review at the review station upon detecting a login, while delaying transfer of remaining studies in the first working set until clinician review of the subset of studies from the first working set at the review station is detected;

after completing transfer of the subset of studies from the first working set to the review station, monitoring the review station for clinician review of the subset of studies from the first working set;

detecting a clinician reviewing the subset of studies from the first working set at the review station; and populating the review station with additional studies from the first working set in response to detecting the clinician reviewing the subset of studies from the first working set at the review station.

8. The one or more computer storage media of claim 7, further comprising distributing the subset of studies from the first working set to each of a plurality of review stations.

9. The one or more computer storage media of claim 7, further comprising implementing a predictive algorithm to identify a set of review stations and distributing the subset of studies from the first working set to the identified review stations.

10. The one or more computer storage media of claim 7, further comprising continuously monitoring the review station to determine if review of a study from the first working set has been completed and removing the study from the first working set after review of the study has been completed at the review station.

11. The one or more computer storage media of claim 10, further comprising deleting the study from at least one other review station in response to determining that review of the study has been completed at the review station.

12. The one or more computer storage media of claim 7, further comprising monitoring the review station for a low buffer threshold and repopulating the review station with an additional subset of studies upon reaching the low buffer threshold.

13. A system for managing studies transferred from at least one acquisition device to a study process server in order to transfer the studies to at least one review station, the system including at least one processor and one or more computer storage media having a plurality of modules embodied thereon, the modules comprising:

a study sorting module that automatically sorts studies received by the study process server from the at least one acquisition device into a plurality of working sets, each working set comprising a collection of studies ready for review by at least one clinician as a set, wherein all studies within each working set are ready for delivery for review by the at least one clinician;

a study distribution module that automatically selects a subset of studies from the first working set and distributes the subset of studies from the first working set to a review station such that the subset of studies from the first working set is available on demand for review by a clinician at the review station, while delaying transfer of remaining studies in the first working set until clinician review of the subset of studies from the first working set at the review station is detected; and a study control module that monitors the review station for clinician review of the subset of studies from the first working set after the subset of studies have been transferred to the review station and causes additional studies from the first working set to be transferred to the review station in response to detecting a clinician reviewing the subset of studies from the first working set at the review station.

14. The system of claim 13, wherein the study distribution module distributes the subset of studies from the first working set to each of a plurality of review stations.

15. The system of claim 13, wherein the study distribution module implements a predictive algorithm to identify a set of review stations and distributes the subset of studies from the first working set to the identified review stations.

16. The system of claim 13, wherein the study control module continuously monitors the review station to determine if review of a study from the first working set has been completed and removes the study from the first working set after review of the study has been completed at the review station.

17. The system of claim 16, wherein the study is deleted from at least one other review station in response to determining that review of the study has been completed at the review station.

18. The system of claim 13, wherein the study control module monitors the review station for a low buffer threshold and re-populates the review station with an additional subset of studies upon reaching the low buffer threshold.

* * * * *